United States Patent [19]

Stein

[11] 4,446,322

[45] May 1, 1984

[54] HYDROXYL PROTECTED 3-(2-HYDROXY-2-PHENYLETHYL)-N-[(PHENYLAMINO)CARBONYL]SYDNONE IMINE INTERMEDIATES

[75] Inventor: Reinhardt P. Stein, Audubon, Pa.

[73] Assignee: American Home Products Corporation, New York, N.Y.

[21] Appl. No.: 193,042

[22] Filed: Oct. 2, 1980

Related U.S. Application Data

[63] Continuation-in-part of Ser. No. 171,423, Jul. 29, 1980, Pat. No. 4,277,609, which is a continuation-in-part of Ser. No. 71,606, Aug. 31, 1979, abandoned.

[51] Int. Cl.³ .................. C07D 295/10; C07D 271/04
[52] U.S. Cl. .................................. 544/138; 544/405; 548/110; 548/125
[58] Field of Search ................ 548/125, 110; 544/138, 544/405

[56] References Cited

U.S. PATENT DOCUMENTS 4,277,609   7/1981   Stein .................................... 548/125

OTHER PUBLICATIONS

Barger, "Medicinal Chemistry," Third Edition, Part 1, (1971) pp. 50–51.

*Primary Examiner*—Anton H. Sutto
*Attorney, Agent, or Firm*—Richard K. Jackson

[57] ABSTRACT

This application provides a novel process for the synthesis of 3-(2-hydroxy-2-phenylethyl)-N-[(phenylamino)carbonyl]sydnonimine derivatives and novel hydrophobic and hydrophilic acyl derivatives thereof as pro-drug central nervous system stimulants.

9 Claims, No Drawings

HYDROXYL PROTECTED 3-(2-HYDROXY-2-PHENYLETHYL)-N-[(PHENYLAMINO)CARBONYL]SYDNONE IMINE INTERMEDIATES

RELATED APPLICATIONS

This application is a continuation-in-part of U.S. patent application Ser. No. 171,423, filed July 29, 1980, now U.S. Pat. No. 4,277,609, which is in turn a continuation-in-part of copending U.S. application Ser. No. 71,606, filed Aug. 31, 1979, now abandoned.

BACKGROUND OF THE INVENTION

After the discovery of the central nervous system stimulatory properties of 3-(1-methyl-2-phenylethyl)-N-(phenylcarbamoyl)-sydnone imine (Sydnocarb; U.S.S.R. No. 329,890 and Offenlegungsschrift No. 2,028,880) various analogues have been reported. U.S.S.R. No. 222,370 and Offenlegungsschrift No. 2,738,022 disclose sydnone imines which contain phenyl, 1- or 2-phenylethyl and the phenylisopropyl groups in 3-position as well as N-meta- and para-chlorophenyl and N-phenyl carbamoyl groups. Variations of 3-benzyl sydnonimines are disclosed in U.S. Pat. No. 3,277,108. Other variously substituted 3-aralkyl sydnonimines are disclosed by Olovyanishinkiva et al., Khim. Geterotsikl Soedin, 2, 170–175 (1978) and 9, 1198–1203 (1975).

Sydnocarb is conventionally produced by cyanomethylation of amphetamine followed by nitrosation and ring closure with a mineral acid to yield sydnophen as an acid halide salt which is reacted with phenylisocyanate under mildly basic conditions to introduce the N-phenylcarbamoyl group. As an asymmetric compound, amphetamine may be employed as the initial reactant as the racemic d,l- mixture or as the pure d- or l-isomer to yield racemic or optically active sydnophen and ultimately sydnocarb.

Yashunskii et al., J. Med. Chem., 14, 1013–1015 (1971) disclose the marked (CNS-stimulatory effect of 3-(1-methyl-2-phenylethyl) sydnonimine (Sydnophen). The relative activities of a large number of alkyl, aryl and aralkylsydnonimines are presented in Table 1 on page 1014. Most of them including compound XVIII (2-hydroxy-1-methyl-2-phenylethyl-sydnonimine), were essentially inactive central nervous system stimulants relative to compound XIII (Sydnophen), demonstrating the criticality of the structure of the 3-substituent in the Sydnocarb series of compounds as far as CNS stimulatory activity is concerned. Thus, although the activity profile of Sydnocarb is not identical to that of amphetamine, or for that matter Sydnophen, CNS stimulatory activity is a common property of the initial reactant amphetamine, the intermediate Sydnophen and the final product Sydnocarb.

Although Sydnocarb and its derivatives disclosed in the literature form salts with various organic and inorganic acids, such salts are not appreciably water soluble and when stirred in water, the complex or adduct salt is broken up to reisolate the neutral mesoionic sydnone imine substrate. The salts of sydnocarb are not true salts, in the classical sense, in that they do not dissociate in water to form water soluble ions consisting of the protonated substrate and the corresponding anion derived from the acidifying agent.

The metabolites of Sydnocarb have been studied by several groups. L. E. Kholodov and E. T. Lilin, Mater. Resp. Rasshir. Konf. Farmacol. Gruz. 2nd 1977, 84–5 report finding hydroxylation of Sydnocarb at the beta carbon of the phenylisopropyl substituent and at the phenyl ring of the phenylcarbamoyl group, hydrolytic cleavage of the phenylcarbamoyl group and ring opening of the heterocyclic nucleus. They report that the psychostimulating activity of Sydnocarb is a property of that compound and not its metabolites. Polgar et al., Acta. Pharm. Hung., 48, Suppl. 23–24 (1978) and Xenobiotica, 9, No. 8, 511–520 (1979) report several hydroxylated metabolites and conjugates of hydroxylated metabolites.

The compounds of my copending application Ser. No. 171,423, now U.S. Pat. No. 4,277,609, were prepared by conventional techniques analogous to those employed in the preparation of Sydnocarb. Thus, a properly substituted phenylethanolamine is cyanomethylated with a reactant $XCH_2CN$ where X may be —OH, —Br, —Cl, tosyl, and the like to form the intermediate:

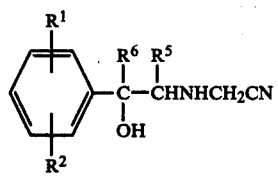

which is nitrosated with an excess of $NaNO_2$ in aqueous HCl to yield the nitroso-nitrile:

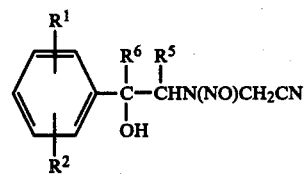

which upon treatment with HCl (anhydrous or in an alkanol, preferably isopropanol) yields the sydnonimine salt:

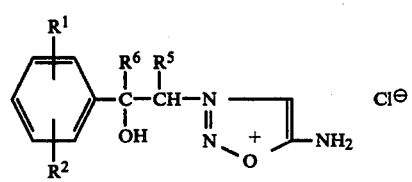

which when reacted as an alcoholic suspension (methanol, ethanol, isopropanol, etc.) with

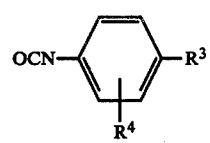

in the presence of a mild base such as sodium acetate yields the desired 3-(2-hydroxy-2-phenylethyl)-N-[(phenylamino)carbonyl]-sydnonimine derivatives.

BRIEF DESCRIPTION OF THE INVENTION

This invention provides (1) an improved process for the production of 3-(2-hydroxy-2-phenylethyl)-N-[(phenylamino)carbonyl]-sydnonimine derivatives disclosed in copending U.S. patent application Ser. No. 171,423, filed July 29, 1980, now U.S. Pat. No. 4,277,609, (2) intermediate compounds produced in that improved process which are in themselves central nervous system stimulants comparable in potency to the final products of said copending application and which afford pro-drugs with hydrophobic or hydrophilic characteristics, and (3) a group of pro-drug compounds which are preparable directly by the process of this invention or from the products of said copending application, Ser. No. 171,423.

DETAILED DESCRIPTION OF THE INVENTION

This invention provides a process for the production of a group of central nervous system stimulants which are 3-(2-hydroxy-2-phenylethyl)-N-[(phenylamino)carbonyl]sydnonimines optionally substituted in either or both phenyl rings of the formula:

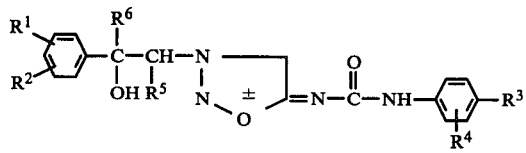

in which the enantiomeric form is d,l- or l- when $R^5$ is hydrogen and d,l- or l-threo when $R^5$ is other than hydrogen;

- $R^1$ and $R^2$ are, independently, hydrogen, alkyl of 1 to 6 carbon atoms, alkoxy of 1 to 6 carbon atoms, halo, perfluoroalkyl of 1 to 3 carbon atoms, nitro, alkanoyl of 2 to 4 carbon atoms, or alkoxycarbonyl of 2 to 4 carbon atoms;
- $R^3$ is hydrogen, halo, nitro or alkanoyl of 2 to 4 carbon atoms;
- $R^4$ is hydrogen, halo, nitro or perfluoroalkyl of 1 to 3 carbon atoms;
- $R^5$ and $R^6$ are, independently, hydrogen or methyl;
- or a non-toxic acid addition salt thereof.

It is generally preferred that the halo substituent be chlorine, bromine or fluorine although iodine is acceptable. Likewise, it is preferred that the alkyl and alkoxy substituents be relatively small, the methyl, ethyl, propyl, isopropyl, methoxy, ethoxy, propoxy and isopropoxy groups being preferred. The $R^3$ substituent in 4 position when $R^4$ is hydrogen influences potency to a greater extent than $R^1$, $R^2$ and $R^4$ and is preferably a halogen. The non-toxic acid addition salts of the compounds are conventionally produced by the method and from any of the acids disclosed in U.S. Pat. No. 3,277,108. The adduct products are preferably formed with hydrochloric, hydrobromic, sulfuric, phosphoric, phosphorous, acetic, propionic, fumeric, oxalic, succinic or maleic acid.

The 3-(2-hydroxy-2-phenylethyl)sydnonimine compounds contain a chiral center at the benzylic carbon atoms and appear as the racemic d,l-mixture which is resolvable into the pure d- and l-isomers. The l-isomer possesses substantially all of the CNS stimulatory activity and is preferred over the racemic mixture for that reason.

The 3-[(2-hydroxy-1-methyl-2-phenylethyl)]sydnonimines and the 3-[(2-hydroxy-2-methyl-1-methyl-2-phenylethyl)]sydnonimines of this invention contain two chiral centers and provide two racemic mixtures of product. Of the four optically active isomers only the l-threo isomer is meaningfully active as a central nervous system stimulant.

It was noted in my cited copending application that in the special situation where the $R^6$ substituent of the benzylic carbon atom of the nitroso-nitrile was other than hydrogen, direct conversion of the intermediate nitroso-nitrile to the final product could be accomplished by reaction with an appropriately substituted aryl isocyanate in the presence of an organic amine base, such as triethylamine, 4-dimethylaminopyridine, and the like, following the procedure disclosed in Offenlegungsschrift No. 2,738,022. However, when $R^6$ is hydrogen, reaction of the nitroso-nitrile with the isocyanate does not give the desired product.

It has now been discovered that all of the 2-hydroxy substituted nitroso-nitrile intermediates disclosed in my said copending application can be directly converted to the desired Sydnocarb derivatives without separate production of the Sydnophen intermediate. Thus, the step of cyclization of the nitroso-nitrile to obtain the Sydnophen intermediate can be completely omitted by the process of this invention.

Hence, in accordance with the first process aspect of this invention, there is provided a method for producing the 3-(2-hydroxy-2-phenylethyl)-N-[(phenylamino)carbonyl]sydnonimines of Formula I, supra, which comprises reacting by nucleophilic addition a compound of the formula:

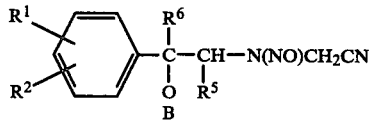

in which B is a hydroxyl protecting group and $R^1$, $R^2$, $R^5$ and $R^6$ are defined above, to an isocyanate of the formula:

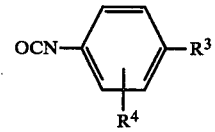

where $R^3$ and $R^4$ are defined above, and subsequently removing the protecting group B.

The hydroxyl protecting groups applicable in the process of this invention are well-known. Exemplary protecting groups are lower alkanoyl of from 1-6 carbon atoms (such as acetyl, propionyl, isopropionyl, etc.), benzoyl, tert-butyl, benzyloxycarbonyl, or silyl ester groups. In selecting a particular hydroxyl protecting group, the criteria for applicability are that the protecting group must be stable during nucleophilic addition to the isocyanate and the protecting group must be removable under reaction conditions which would not otherwise affect the molecule and preferably, where the protecting group is to be retained for use of the compound as a pro-drug, its metabolite should produce no untoward effect. Based upon those standards, the preferred protecting groups are the lower alkanoyl groups. When production of a pro-drug is not desired, it is preferred that the protecting group B be selected to achieve rapid deprotection during and as a result of normal work-up procedures following production of the desired compound. The trimethylsilyl group is ideal for this purpose, (although other known silyl protecting groups may be used) because N,O-bis(trimethylsilyl-)acetamide is readily available, requires no acid acceptor during reaction with the hydroxyl group, affords neutral or volatile by-products of the silylation reaction and is removed in the normal work-up of the desired product by treatment with an acid to obtain the water-insoluble non-toxic acid addition salt of the Sydnocarb derivative.

Other applicable silyl esters are those tertiary ($R_3Si—$) and secondary ($R_2Si—$) silyl moieties in which R is lower alkyl, aryl (preferably the phenyl group) or aralkyl (preferably the phenyl(lower)alkyl group and more preferably benzyl). The tri(lower)alkylsilyl groups being preferred because they are readily hydrolyzed with an alcohol or water to release the free hydroxy substituted product.

Protection of the beta-hydroxy group, when effected with conventional acylating agents such as acetyl chloride, acetic anhydride, and the like, requires the use of at least one equivalent of the acylating agent and one equivalent of an organic base acid receptor such as pyridine. The use of a silyl ester protecting group does not require an acid acceptor. Deprotection is accomplished with a mild base such as sodium or potassium carbonate in protic solvent or with an acid in the case of silyl ester protection.

Thus, as the intermediate compound aspect of this invention there is provided a group of compounds of the formula:

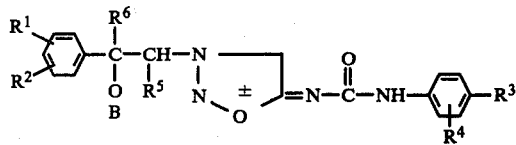

in which $R^1$ to $R^6$ are defined above;

and B is a hydroxyl protecting group.

As mentioned previously, certain hydroxy protected sydnocarb derivatives are directly useful as anti-depressants in that they are equal in activity to the free hydroxy substituted final products. These protected sydnocarb derivatives serve as pro-drugs in that the protecting group is enzymatically removed in vivo to release the free β-hydroxy sydnocarb derivatives as CNS stimulants. These protected β-hydroxy sydnocarb derivatives form an additional compound aspect of the invention.

Thus, embraced by formula II are certain pro-drugs such as those in which B is alkanoyl of 1 to 6 carbon atoms, tert-butyl or benzoyl.

In addition, a unique group of pro-drugs reside in beta hydroxy protected sydnocarb derivatives in which the hydroxy protecting groups are amino substituted acyl moieties such as are represented by the formula:

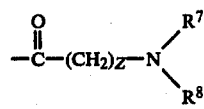

in which

Z is an integer from 1 to 6;

$R^7$ is alkyl of 1 to 6 carbon atoms or aralkyl of 7 to 16 carbon atoms;

$R^8$ is alkyl of 1 to 6 carbon atoms, aralkyl of 7 to 16 carbon atoms, dialkylaminoalkyl of 3 to 18 carbon atoms or diaralkylaminoalkyl of 14 to 32 carbon atoms;

or $R^7$ and $R^8$ are concatenated to form the 4-morpholinyl moiety or a radical of the formulae:

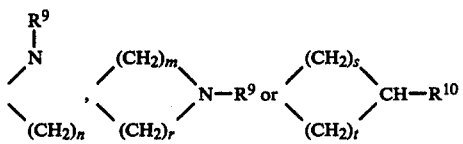

wherein $R^9$ is alkyl of 1 to 6 carbon atoms, aryl of 6 to 10 carbon atoms, hydroxyalkyl of 1 to 6 carbon atoms; aralkyl of 7 to 16 carbon atoms or alkoxyalkyl of 2 to 12 carbon atoms; $R^{10}$ is alkylamino of 1 to 6 carbon atoms or piperidino; n is one of the integers 3, 4 or 5; m is one of the integers 1 or 2; r is one of the integers 2 or 3; s is an integer from 0 to 6; t is an integer from 0 to 6; with the proviso that the sum of s and t is 3 to 6; or a pharmaceutically acceptable salt thereof.

The salts of the aminoacyloxy protected sydnocarb derivatives are water soluble and therefore amenable to administration via an aqueous vehicle. The non-water soluble salt forming and hydrophobic substituted beta-hydroxy sydnocarb pro-drug derivatives are administerable either neat or via suspension or emulsions for lipophilic assimilation and in vivo conversion to the free hydroxy substituted stimulants.

Where desired, the pro-drug compounds embraced by formula II may be produced directly from the final product β-hydroxy sydnocarb derivatives disclosed in U.S. Pat. No. 4,277,609. Thus, the β-hydroxy sydnocarb derivatives may be directly acylated with the desired acyl group to obtain the desired pro-drug. With the aminoacyl protecting groups, an indirect preparatory technique may be employed. For example, chloroacetylation of a beta-hydroxy sydnocarb derivative provides an intermediate in which the amino substituent may be tailored as desired. Thus, the chloroacetylated product is reacted with a desired mono-amine or di-amine (such as those disclosed in U.S. Pat. No. 3,886,276 from which the disclosure of applicable di-amines is incorporated herein by reference) to afford amino acetate esters of the β-hydroxy sydnocarb derivatives from which pharmaceutically acceptable water-soluble salts are produced. Unlike the Sydnone imine salts of the prior art, the salts formed with the aminoacetate esters of the hydroxy substituted Sydnone imine derivatives of this invention are water soluble, dissociating sufficiently to dissolve in aqueous medium to provide a homogenous solution. Thus, the salts of the aminoacylated beta hydroxy sydnocarb derivatives may be formulated for administration in aqueous vehicle thereby expanding the routes available for practical dosing to achieve central nervous system stimulation to patients unable to receive treatment orally.

The activity profile of the pro-drug compounds of this invention is similar to that of amphetamine in some aspects while being devoid of other activities of amphetamine. For example, like amphetamine the pro-drug compounds of this invention increase motor activity. However, the pro-drug compounds of this invention are much less toxic than amphetamine, providing a slower onset of activity (which indicates less euphoria and abuse potential).

The pro-drug compounds of this invention were shown to possess central nervous system stimulant activity by subjecting them to the following standard test procedure:

Male mice weighing 17 to 25 gms. are injected orally with drug solubilized or suspended in 1% Tween ® 80. Control animals are injected with 1% Tween ® 80.

Six Columbus Instrument Company activity chambers are employed. Three mice given identical treatment are placed in each chamber for all tests. During each run, control animals (1% Tween ® only) occupy 3 chambers; the other 3 chambers measure activity of drug treated animals. For each dose of a given drug the experiment is run two times in a counterbalanced design so that each specific activity chamber records the activity of control animals during one run, and the activity of drug animals on the other run. Thus, at each dose level 18 mice are used in the drug group and 18 mice in the control group.

Activity counts are recorded every ten minutes for a period of 2 hours. The data are analyzed using Students "t" test comparing the means of the control and drug groups for each 10 minute period. The drug treated group is compared graphically with the control group in regard to duration of action and dose response at peak drug activity.

As central nervous system stimulants with unique activity profiles, the pro-drug compounds of this invention are useful in the treatment of anergic disorders (such as sleepiness and fatigue) including related types of depression and narcolepsy. Based upon the potency of the compounds of this invention in use in mice, the dose contemplated for use in the 70 kilogram human would vary from about 35-700 milligrams administered orally once or twice per day under the guidance of a physician. Of course, the dosage regimen as well as the route of administration, oral or parenteral, will vary with the condition of the patient relative to age, severity of depression, etc.

The following examples illustrate, without limitation, the novel process for producing the β-hydroxy sydnocarb derivatives of my copending application Ser. No. 171,423, now U.S. Pat. No. 4,277,609, the intermediates formed in that process, the hydroxy substituted pro-drug compounds and the direct production of those pro-drug compounds from the products disclosed in said copending application. Activity counts represent the difference from control. 1-Sydnocarb presents a difference from control of 939 counts at 10 mg/kg.

EXAMPLE 1

1-[[2-(Acetyloxy)-2-Phenylethyl]-Nitrosoamino]Acetonitrile

Dissolve 1-[(2-hydroxy-2-phenylethyl)nitrosoamino]acetonitrile (2.16 g.) in methylene chloride (25 ml.). Add pyridine (2.40 g.) followed by acetic anhydride (3.06 g.). Let the reaction stand at room temperature overnight. Wash with 2 N aqueous HCl, saturated sodium bicarbonate solution, and brine. Dry, then evaporate the solvent in vacuo. Pump, then dissolve the residue in diethyl ether and let stand to crystallize. Filter to obtain 1.55 g.; m.p. 89°-91° C. Dissolve the solid in methylene chloride, treat with decolorizing carbon, filter and evaporate the solvent in vacuo. Dissolve the oil in diethyl ether and let stand to crystallize. Filter to obtain 1.26 g. of the pure title product; m.p. 90°-91.5° C.; $[\alpha]_D^{25.5} = -92.18°$ (1.00% in methanol).

Analysis for: $C_{12}H_{13}N_3O_3$: Calculated: C, 58.29; H, 5.30; N, 17.00. Found: C, 58.20; H, 5.30; N, 17.16.

EXAMPLE 2

1-N-[[(4-Chlorophenyl)Amino]Carbonyl]-3-(2-Hydroxy-2-Phenylethyl)Sydnone Imine

Stir 1-[[2-(acetyloxy)-2-phenylethyl]nitrosoamino]acetonitrile (4.685 g.) with toluene (100 ml.), then add triethylamine (1.923 g.) followed by 4-chlorophenylisocyanate (2.918 g.) and stir at room temperature overnight. Add another 2.00 g. of 4-chlorophenylisocyanate and continue stirring at room temperature overnight. Filter and evaporate the filtrate in vacuo. Dissolve the resulting oil, 1-3-(2-acetyloxy-2-phenylethyl)-N-(4-chlorophenylaminocarbonyl)-Sydnone imine in methanol (150 ml.), add anhydrous powdered sodium carbonate (2.00 g.) and stir for 2 hours at room temperature. Add water (total 250 ml.) dropwise with stirring, filter the resulting solid and wash well with water. Air-dry the solid, then cover with diethyl ether and stir for 1 hour at room temperature. Filter and dry the solid to get 3.103 g. of the crude title product; m.p. 173.5°-175° C. (dec.). Boil the solid with a mixture of methylene chloride, methanol and acetone until nearly clear, filter, then replace the solvents with isopropanol by boiling on the steam-bath. Let stand to crystallize, then filter to obtain 2.127 g. of title product; m.p. 179°-181° C. Repurify the solid as above to obtain 1.381 g. of title product; m.p. 182°-184° C. (dec.); $[\alpha]_D^{23} = -61.50°$ (1.015% in DMF).

EXAMPLE 3

1-N-[[(4-Chlorophenyl)Amino]Carbonyl]-3-(2-Hydroxy-2-Phenylethyl)Sydnone Imine

Stir 1-[(2-hydroxy-2-phenylethyl)nitrosoamino]acetonitrile (2.540 g.) with toluene (75 ml.), add N,O-bis(trimethylsilyl)-acetamide (7.55 g.) and stir for 2 hours at room temperature. Evaporate the solvent in vacuo and pump to remove the silylation reagents and by-products. Redissolve the oil in toluene (75 ml.), stir and add 4-chlorophenylisocyanate (2.10 g.) followed by triethylamine (1.38 g.). Stir at room temperature, then let stand for 3 days. Filter, evaporate the filtrate in vacuo and pump to obtain 1-N-(4-chlorophenylaminocarbonyl)-3-(2-trimethylsilyloxy-2-phenylethyl)sydnone imine as an oil. Dissolve the oil in ethyl acetate and stir for 3 hours with excess 2 N aqueous HCl. Filter and dry to obtain 0.410 g. of the title product as a hydrochloride; m.p. 189°-190° C. (dec.). Separate the ethyl acetate layer from the filtrate, wash with water, brine and dry. Evaporate the solvent in vacuo. Cover the resulting oil with diethyl ether and a little isopropanol and let stand to crystallize. Filter to obtain 0.723 g. of the crude title product; m.p. 169°-178° C. Boil the solid to dissolve in a mixture of methylene chloride-methanol-acetone, filter, then replace the sol-

EXAMPLE 4

1-[[2-(Chloroacetyloxy)-2-Phenylethyl]Nitrosoamino]Acetonitrile

Dissolve 1-[(2-hydroxy-2-phenylethyl)nitrosoamino]acetonitrile (1.025 g.) in methylene chloride (10 ml.), add pyridine (1.19 g.) followed by chloroacetic anhydride (2.56 g.), swirl to dissolve, then let stand overnight. Wash the solution with 2 N aqueous HCl, with water, saturated sodium bicarbonate solution, brine and dry. Evaporate the solvent, add diethylether and triturate to obtain 0.792 g. of crude product; m.p. 110°–115° C. Digest the solid with chloroform and pass through a short column of activated silica gel. Elute with chloroform and evaporate the chloroform in vacuo. Triturate the solid with diethylether and filter to obtain 0.616 g. of the pure title product; m.p. 118°–120° C.; $[\alpha]_D^{23} = -116.65°$ (1.085% in methanol).

Analysis for: $C_{12}H_{12}ClN_3O_3$: Calculated: C, 51.16; H, 4.30; N, 14.92. Found: C, 50.88; H, 4.10; N, 14.95.

EXAMPLE 5

1-N-[[(4-Chlorophenyl)Amino]Carbonyl]-3-[2-(Diethylaminoacetyloxy)-2-Phenylethyl]Sydnone Imine, Dihydrochloride Stir 1-[[2-(chloroacetyloxy)-2-phenylethyl]nitrosoamino]acetonitrile (5.64 g.) with tetrahydrofuran (150 ml.), add triethylamine (6.07 g.) followed by diethylamine (4.39 g.), then stir under nitrogen overnight. Add tetrabutylammonium iodide (100 mg.) and continue stirring overnight. Filter, evaporate the filtrate in vacuo, then dissolve the oil in methylene chloride. Wash, dry and evaporate the extract in vacuo. Dissolve the resulting 1-[[2-(diethylaminoacetyloxy)-2-phenylethyl]nitrosoamino]acetonitrile as an oil in 1,2-dimethoxyethane (100 ml.), add triethylamine (2.02 g.) followed by 4-chlorophenylisocyanate (3.07 g.) and stir at room temperature for 24 hours. Add another 2.0 g. of 4-chlorophenylisocyanate and stir overnight. Filter, evaporate the solvent in vacuo and dissolve the resulting oil in methylene chloride. Cool and treat with excess 5 N isopropanolic-HCl (12 ml.). Evaporate the solvents in vacuo. Digest the residue with water, filter, then add methylene chloride to the filtrate. Treat the mixture portionwise with solid anhydrous sodium carbonate (7.4 g.) with shaking. Extract with methylene chloride, then wash, dry and evaporate the combined extracts in vacuo. Pump the oil dry, then redissolve in methylene chloride and treat with excess 5 N isopropanolic-HCl (12 ml.) with cooling. Evaporate the solvents in vacuo. Dissolve the residue in acetonitrile and let stand to crystallize. Filter to obtain 2.000 g. of the title product; m.p. 185°–186° C. (dec.). Dissolve the solid in methylene chloride-methanol, treat with decolorizing carbon, filter, then evaporate the solvents in vacuo. Triturate the residue with hot acetonitrile, cool and filter to obtain 1.691 g. of the pure title product as the hydrate; m.p. 185°–187° C. (dec.); $[\alpha]_D^{26.5} = -55.14°$ (1.03% in methanol).

Analysis for: $C_{23}H_{26}ClN_5O_4.2HCl.H_2O$: Calculated: C, 49.07; H, 5.37; N, 12.44. Found: C, 49.02; H, 5.12; N, 12.93. Activity Counts: 586 p<0.01 at 10 mg/kg.

EXAMPLE 6

1-3-[2-(Chloroacetyloxy)-2-Phenylethyl]-N-[(Phenylamino)-Carbonyl]Sydnone Imine

Stir 1-3-(2-hydroxy-2-phenylethyl)-N-[(phenylamino)carbonyl]sydnone imine (7.26 g.) with tetrahydrofuran (150 ml.), then cool, and with stirring add 4-dimethylaminopyridine (2.73 g.) followed by dripping in a solution of chloroacetylchloride (2.53 g.) in tetrahydrofuran (25 ml.). Continue stirring at room temperature for 3 hours. Filter, evaporate the solvent from the filtrate in vacuo, then treat the residue in methylene chloride with decolorizing carbon. Filter, evaporate in vacuo and pump the residue to obtain the title product as a glass sufficiently pure for all subsequent reactions.

EXAMPLE 7

1-3-[2-[(4-Methyl-1-Piperazinyl)Acetyloxy]-2-Phenylethyl]-N-[(Phenylamino)Carbonyl]Sydnone Imine, Trihydrochloride Dissolve 1-3-[2-(chloroacetyloxy)-2-phenylethyl]-N-[(phenylamino)carbonyl]sydnone imine (6.90 g.) in tetrahydrofuran (100 ml.), stir, and add triethylamine (1.74 g.) followed by N-methylpiperazine (1.73 g.) using tetrahydrofuran to rinse in the reagents. Stir at room temperature for 3 hours, then let stand overnight. Stir a further 6 hours, then evaporate the solvent in vacuo. Dissolve the residue in methylene chloride, wash with brine, water, then brine again. Dry and evaporate the extract in vacuo and pump dry. Redissolve the residue in methylene chloride, add excess 5 N isopropanolic-HCl (12 ml.). Evaporate in vacuo and pump to a solid. Cover and tirturate with water, add a little methylene chloride, then separate the layers. Treat the water layer with decolorizing carbon, filter, cool, then drip in 10% potassium carbonate solution until a pH of 9 is reached. Quickly extract with methylene chloride, then wash with water and brine. Evaporate the solvent in vacuo and pump to a glass. Dissolve the glass in acetonitrile, add 5 N isopropanolic-HCl (5 ml.) and evaporate in vacuo. Cover the residue with a little acetonitrile, warm, then cool and triturate the solid. Let the solid settle, decant the acetonitrile and add fresh acetonitrile, then tirturate the solid again. Filter and dry to obtain 1.70 g. of the title product as a partial hydrate; m.p. 185°–187° C. (dec.); $[\alpha]_D^{25} = -60.02°$ (1.11% in methanol).

Analysis for: $C_{24}H_{28}N_6O_4.3HCl.2/3H_2O$: Calculated: C, 49.19; H, 5.56; N, 14.34; Cl, 18.15. Found: C, 49.18; H, 5.57; N, 14.52; Cl, 17.96. Activity Counts: 946: p<0.01 at 10 mg/kg.

EXAMPLE 8

1-3-[2-(4-Morpholinylacetyloxy)-2-Phenylethyl]-N-[(Phenylamino)-Carbonyl]Sydnone Imine, Dihydrochloride Dissolve 1-3-[2-chloroacetyloxy)-2-phenylethyl]-N-[(phenylamino)carbonyl]sydnone imine (5.01 g.) in tetrahydrofuran (100 ml.), add triethylamine (1.40 g.) following by morpholine (1.20 g.) using tetrahydrofuran to rinse in the reagents. Stir for 3 hours at room temperature, then let stand overnight. Evaporate the solvent in vacuo, dissolve the residue in methylene chloride, then wash, dry and evaporate the solvent in vacuo. Pump the residue to a dry glass. Dissolve the glass in methylene chloride, treat with 5 N isopropanolic-HCl (5 ml.), evaporate the solvents in vacuo and pump to a glass. Cover the residue with water, triturate well, then treat the mixture with decolorizing carbon and filter. Add methylene chloride to the water layer followed by solid potassium carbonate (4.0 g.), then shake to quickly extract the product. Further extract the water layer with methylene chloride, then wash, dry and evaporate the combined extracts in vacuo. Pump the residue to a dry glass. Dissolve the glass in methylene chloride, treat with decolorizing carbon and filter. Treat the solution with 5 N isopropanolic-HCl (5 ml.) and evaporate the solvents in vacuo. Add a little methylene chloride and scratch to induce crystallization letting the solvent evaporate. Cover with acetone, triturate the solid and filter to obtain 1.79 g. of title product; m.p. 146°–150° C. (dec.). Dissolve the solid in methylene chloride containing a little methanol, treat with decolorizing carbon, filter, then evaporate in vacuo to a gum. Add isopropanol and a little methanol to solubilize. Remove the solvents in vacuo and in the cold to obtain a solid. Triturate the solid with isopropanol and filter to obtain 1.18 g. of the pure title product; m.p. 168°–172° C. (dec.); $[\alpha]_D^{25} = -59.57°$ (1.05% in methanol).

Analysis for: $C_{23}H_{25}N_5O_5 \cdot 2HCl$: Calculated: C, 52.68; H, 5.19; N, 13.36; Cl, 13.52. Found: C, 52.43; H, 4.99; N, 13.53; Cl, 13.17. Activity Counts: 1010 p<0.01 at 10 mg/kg.

EXAMPLE 9

1-3-[2-(Diethylaminoacetyloxy)-2-Phenylethyl]-N-[(Phenylamino)Carbonyl]Sydnone Imine, Dihydrochloride Dissolve the glassy 1-3-[2-(chloroacetyloxy)-2-phenylethyl]-N-[(phenylamino)carbonyl]sydnone imine (5.01 g.) in tetrahydrofuran (100 ml.), add triethylamine (1.51 g.) followed by diethylamine (1.10 g.) using tetrahydrofuran to rinse in the reagents. Stir for 2 hours at room temperature, then let stand for several days. Filter, evaporate the solvent in vacuo and dissolve the oil in methylene chloride. Wash, dry and evaporate the solvent in vacuo. Pump the residue to a dry glass. Dissolve the glass in methylene chloride, add 5 N isopropanolic-HCl (5 ml.), then evaporate in vacuo and pump to a glass. Cover with water, triturate, treat with decolorizing carbon and filter. Add methylene chloride to the aqueous layer followed by solid potassium carbonate (3.50 g.). Quickly shake and separate the layers. Wash, dry and evaporate the methylene chloride in vacuo. Treat the residue in methylene chloride with decolorizing carbon, filter, then treat the filtrate with 5 N isopropanolic-HCl (5 ml.). Evaporate the solvents in vacuo and pump to dry the product. Dissolve in acetonitrile and let stand to crystallize. Filter and dry the solid to obtain 1.27 g. of the pure title product; m.p. 174°–176° C. (dec.); $[\alpha]_D^{25} = -55.31°$ (0.99% in methanol).

Analysis for: $C_{23}H_{27}N_5O_4 \cdot 2HCl$: Calculated: C, 54.12; H, 5.73; N, 13.72; Cl, 13.89. Found: C, 54.01; H, 5.66; N, 14.09; Cl, 13.76. Activity Counts: 720 p<0.01 at 10 mg/kg.

EXAMPLE 10

1-3-[2-(Chloroacetyloxy)-2-Phenylethyl]-N-[[(4-Chlorophenyl)-Amino]Carbonyl]Sydnone Imine Stir 1-N-[[(4-chlorophenyl)amino]carbonyl]-3-(2-hydroxy-2-phenylethyl)sydnone imine (3.59 g.) with chloroform (150 ml.), add pyridine (2.37 g.) followed by chloroacetic anhydride (5.13 g.) and continue stirring for ½ hour. Quench the reaction by stirring with 2 N aqueous HCl (100 ml.). Wash the chloroform layer with 2 N aqueous HCl, water, saturated sodium bicarbonate solution, brine, then dry and evaporate the extract in vacuo. Cover the oil with diethyl ether containing some isopropanol to dissolve the oil, let crystallize, then filter to obtain 2.512 g. of the crude title product: m.p. 128°–135° C. Dissolve the solid in methylene chloride, treat with decolorizing carbon, filter, then evaporate the solvent in vacuo. Dissolve the residue in warm-isopropanol, add a little ether to remove cloudiness, filter, then let stand to crystallize to obtain 1.732 g.; m.p. 132°–137° C. Dissolve the solid in methylene chloride, evaporate in vacuo and dissolve the resulting glass in diethylether. Let stand, then filter to obtain 1.449 g. of the pure title product; m.p. 133°–136° C.; $[\alpha]_D^{25} = -97.36°$ (1.015% in methanol).

Analysis for: $C_{19}H_{16}Cl_2N_4O_4$: Calculated: C, 52.43; H, 3.71; N, 12.87. Found: C, 52.54; H, 3.81; N, 13.05.

EXAMPLE 11

1-N-[[(4-Chlorophenyl)Amino]Carbonyl]-3-[2-(Diethylaminoacetyloxy)-2-Phenylethyl]Sydnone Imine, Dihydrochloride Dissolve 1-3-[2-(chloroacetyloxy)-2-phenylethyl]-N-[[(4-chlorophenyl)amino]carbonyl]sydnone imine (3.478 g.) in tetrahydrofuran (50 ml.), add triethylamine (0.97 g.) followed by diethylamine (0.71 g.). Stir, then let the reaction stand at room temperature overnight. Add another 0.97 g. of triethylamine and another 0.71 g. of diethylamine, stir and let the reaction stand overnight. Filter, evaporate the solvent in vacuo, then dissolve the resulting oil in methylene chloride and wash, dry and evaporate the solvent in vacuo. Pump dry, then dissolve the residue in methylene chloride, treat with excess 5 N isopropanolic-HCl (5 ml.) and evaporate the solvents in vacuo. Triturate the resulting solid with acetonitrile, filter and dry to obtain 3.16 g. of the crude title product. Dissolve the solid in methylene chloride-methanol, treat with decolorizing carbon, filter, then evaporate the solvents to low volume in vacuo. Add acetonitrile and boil to remove the methylene chloride and methanol. Let stand, then filter and dry to obtain 2.228 g. of the title product as the anhydrous form of the product of Example 5; m.p. 190°–193° C. (dec.). $[\alpha]_D = -50.8°$ (1.00% in methanol).

Analysis for: $C_{23}H_{26}ClN_5O_4 \cdot 2HCl$: Calculated: C, 50.70; H, 5.18; N, 12.85. Found: C, 50.66; H, 5.08; N, 13.19.

What is claimed is:

1. A hydroxyl protected 3-(2-hydroxy-2-phenylethyl)-N-[(phenylamino)carbonyl]sydnone imine derivative of the formula:

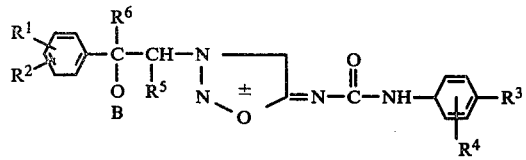

in which the enantiomeric form is d,l or l when $R^5$ is hydrogen and d,l-threo or l-threo when $R^5$ is other than hydrogen;

$R^1$ and $R^2$ are, independently, hydrogen, alkyl of 1 to 6 carbon atoms, alkoxy of 1 to 6 carbon atoms halo, perfluoroalkyl of 1 to 3 carbon atoms, nitro, alkanoyl of 2 to 4 carbon atoms, or alkoxycarbonyl of 2 to 4 carbon atoms;

$R^3$ is hydrogen, halo, nitro or alkanoyl of 2 to 4 carbon atoms;

$R^4$ is hydrogen, halo, nitro or perfluoroalkyl of 1 to 3 carbon atoms;

$R^5$ and $R^6$ are, independently, hydrogen or methyl; and B is a hydroxy protecting group.

2. A hydroxyl protected compound of claim 1 in which B is alkanoyl of 2 to 6 carbon atoms, benzoyl, tert-butyl, benzyloxycarbonyl or silyl ester group.

3. The compound of claim 2 which is 3-(2-acetyloxy-2-phenylethyl)-N-[(4-chlorophenylamino)carbonyl]-sydnonimine or a non-toxic acid addition salt thereof.

4. The compound of claim 2 which is 3-(2-trimethylsilyloxy-2-phenylethyl)-N-[(4-chlorophenylamino)carbonyl]sydnonimine.

5. A compound of claim 1 which is 3-(2-aminoacyloxy-2-phenylethyl)-N-[(phenylamino)carbonyl]sydnone imine derivative of the formula:

[chemical structure]

in which the enantiomeric form is d,l or l when $R^5$ is hydrogen and d,l-threo or l-threo when $R^5$ is other than hydrogen;

$R^1$ and $R^2$ are, independently, hydrogen, alkyl of 1 to 6 carbon atoms, alkoxy of 1 to 6 carbon atoms, halo, perfluoroalkyl of 1 to 3 carbon atoms, nitro, alkanoyl of 2 to 4 carbon atoms or alkoxycarbonyl of 2 to 4 carbon atoms;

$R^3$ is hydrogen, halo, nitro or alkanoyl of 2 to 4 carbon atoms;

$R^4$ is hydrogen, halo, nitro or perfluoroalkyl of 1 to 3 carbon atoms;

$R^5$ and $R^6$ are, independently, hydrogen or methyl;

Z is an integer from 1 to 6;

$R^7$ is alkyl of 1 to 6 carbon atoms or aralkyl of 7 to 16 carbon atoms;

$R^8$ is alkyl of 1 to 6 carbon atoms, aralkyl of 7 to 16 carbon atoms, dialkylaminoalkyl of 3 to 18 carbon atoms or diaralkylaminoalkyl of 14 to 32 carbon atoms;

or $R^7$ and $R^8$ are concatenated to form the 4-morpholinyl moiety or a radical of the formulae:

[chemical structure]

wherein $R^9$ is alkyl of 1 to 6 carbon atoms, aryl of 6 to 10 carbon atoms, hydroxyalkyl of 1 to 6 carbon atoms; aralkyl of 7 to 16 carbon atoms or alkoxyalkyl of 2 to 12 carbon atoms; $R^{10}$ is alkylamino of 1 to 6 carbon atoms or piperidino; n is one of the integers 3, 4 or 5; m is one of the integers 1 or 2; r is one of the integers 2 or 3; s is an integer from 0 to 6; t is an integer from 0 to 6; with the proviso that the sum of s and t is 3 to 6; or a pharmaceutically acceptable salt thereof.

6. The compound of claim 5 which is 1-3-[2-[(4-methyl-1-piperazinyl)acetyloxy]-2-phenylethyl]-N-[(phenylamino)carbonyl]sydnone imine or a pharmaceutically acceptable salt thereof.

7. The compound of claim 5 which is 1-3-[2-(4-morpholinylacetyloxy)-2-phenylethyl]-N-[(phenylamino)carbonyl]sydnone imine or a pharmaceutically acceptable salt thereof.

8. The compound which is 1-3-[2-(diethylaminoacetyloxy)-2-phenylethyl]-N-[(phenylamino)carbonyl]sydnone imine or a pharmaceutically acceptable salt thereof.

9. The compound of claim 5 which is 1-N-[[(4-chlorophenyl)-amino]carbonyl]-3-[2-(diethylaminoacetyloxy)-2-phenylethyl]sydnone imine or a pharmaceutically acceptable salt thereof.

* * * * *